United States Patent
Karlsson et al.

(10) Patent No.: US 6,582,947 B1
(45) Date of Patent: Jun. 24, 2003

(54) MEDICAL USE OF GENE AND VECTOR ENCODING A MULTISUBSTRATE DEOXYRIBONUCLEOSIDE KINASE

(75) Inventors: Anna Karlsson, Stockholm (SE); Magnus Johansson, Solna (SE)

(73) Assignee: BIO VICI, Lausanne (CH)

( * ) Notice: Subject to any disclaimer, the term of this patent is extended or adjusted under 35 U.S.C. 154(b) by 0 days.

(21) Appl. No.: 09/857,498

(22) PCT Filed: Dec. 10, 1999

(86) PCT No.: PCT/SE99/02314
§ 371 (c)(1),
(2), (4) Date: Jun. 19, 2001

(87) PCT Pub. No.: WO00/36099
PCT Pub. Date: Jun. 22, 2000

(30) Foreign Application Priority Data

Dec. 11, 1998 (SE) ................................................ 9804298

(51) Int. Cl.⁷ ......................... C12N 9/12; C12N 15/54; A61K 31/7088
(52) U.S. Cl. ................. 435/194; 435/235.1; 435/320.1; 536/23.2; 424/93.2; 514/44
(58) Field of Search ............................. 435/320, 235.1, 435/194; 536/23.2; 424/93.2; 514/44

(56) References Cited

PUBLICATIONS

The Journal of Biological Chemistry, vol. 273, No. 7, Feb. 1998, Birgitte Munch–Petersen et al.; "Four Deoxynucleoside Kinase Activities from *Drosphila melanogaster* Are Contained within a Single Monomeric Enzyme, a New Multifunctional Deoxynculeoside Kinase" pp. 3926–3931.

Advan. enzyme Regul., vol. 34, 1994, Staffan Eriksson et al.; "Properties and levels of deoxynucleoside kinases in normal and tumor cells; implications for chemotherapy" pp. 13–25.

*Primary Examiner*—Charles L. Patterson, Jr.
(74) *Attorney, Agent, or Firm*—Nixon & Vanderhye P.C.

(57) ABSTRACT

By inserting a DNA or RNA sequence comprising a subsequence showing a homology of at least 60%, preferably at least 80%, and most preferably at least 90% of the DNA sequence of SEQ. ID. NO. 1 into a cell, that cell will obtain a broad specificity for changing nucleoside analog prodrugs to active drugs by phosphorylation. Likewise this changement will occur at a high catalytic rate. Preferably the DNA sequence is inserted into the cell by transformation with a suitable virus or another suitable vector. Such viruses and vectors also constitute a part of the present invention.

19 Claims, 6 Drawing Sheets

SEQUENCE LISTING

<160> NUMBER OF SEQ ID NOS: 8

<210> SEQ ID NO 1
<211> LENGTH: 1113
<212> TYPE: DNA
<213> ORGANISM: Drosophila melanogaster

<400> SEQUENCE: 1

| | | | | | |
|---|---|---|---|---|---|
| ccatcgaatc | cggaacaatc | aacttcaacc | gcgatccgtt | gctgctgtgc | tgtacctaaa | 60 |
| acagttagta | aaactcccaa | tctcacgtgc | agatcgccga | ttatccggac | tgatggcgga | 120 |
| ggcagcatcc | tgtgcccgaa | aggggaccaa | gtacgccgag | ggcacccagc | ccttcaccgt | 180 |
| cctcatcgag | ggcaacatcg | gcagcgggaa | gaccacgtat | ttgaaccact | tcgagaagta | 240 |
| caagaacgac | atttgcctgc | tgaccgagcc | cgtcgagaag | tggcgcaacg | tcaacggggt | 300 |
| aaatctgctg | gagctgatgt | acaagatccc | aagaagtgg | gccatgccct | ttcagagtta | 360 |
| tgtcacgctg | accatgctgc | agtcgcacac | cgccccaacc | aacaagaagc | taaaaataat | 420 |
| ggagcgctcc | attttagcg | ctcgctattg | cttcgtggag | aacatgcgac | gaaacggctg | 480 |
| gctggagcag | ggcatgtaca | atacgctgga | ggagtggtac | aagttcatcg | aagagtccat | 540 |
| tcacgtgcag | gcggacctca | tcatatatct | gcgcacctcg | ccggaggtgg | cgtacgaacg | 600 |
| catccggcag | cgggctcgtt | ctgaggagag | ctgcgtgccg | cttaagtacc | ttcaggagct | 660 |
| gcatgagttg | cacgaggact | ggttgataca | ccagagacga | ccgcagtcgt | gcaaggtcct | 720 |
| agtcctcgat | gccgatctga | acctggaaaa | cattggcacc | gagtaccagc | gctcggagag | 780 |
| cagcatattc | gacgccatct | caatgaacca | acagccctcg | ccggttctgg | tgtcgcccag | 840 |
| caagcgccag | agggtcgcca | gataaccatt | atcccattag | tacctaattg | tgtgtagtac | 900 |
| agacgtttaa | aataatatta | taagaggcct | agacgagccg | attcgcggga | caaaggcaga | 960 |
| aacttacact | tcgagccaat | gattaacaca | ttcgtatatt | aacaattata | atccacatta | 1020 |
| tattctcttc | acagcaacta | gtatgtaagc | tcaaaatatt | gtaataaaaa | ctgtgaatgt | 1080 |
| ttatgttaaa | ggcaaaaaaa | aaaaaaaaaa | aaa | | | 1113 |

<210> SEQ ID NO 2
<211> LENGTH: 250
<212> TYPE: PRT
<213> ORGANISM: Drosophila melanogaster

<400> SEQUENCE: 2

Met Ala Glu Ala Ala Ser Cys Ala Arg Lys Gly Thr Lys Tyr Ala Glu
 1               5                  10                  15

Gly Thr Gln Pro Phe Thr Val Leu Ile Glu Gly Asn Ile Gly Ser Gly
             20                  25                  30

Lys Thr Thr Tyr Leu Asn His Phe Glu Lys Tyr Lys Asn Asp Ile Cys
         35                  40                  45

Leu Leu Thr Glu Pro Val Glu Lys Trp Arg Asn Val Asn Gly Val Asn
     50                  55                  60

Leu Leu Glu Leu Met Tyr Lys Asp Pro Lys Lys Trp Ala Met Pro Phe
 65                  70                  75                  80

Gln Ser Tyr Val Thr Leu Thr Met Leu Gln Ser His Thr Ala Pro Thr
                 85                  90                  95

Asn Lys Lys Leu Lys Ile Met Glu Arg Ser Ile Phe Ser Ala Arg Tyr
            100                 105                 110

```
Cys Phe Val Glu Asn Met Arg Arg Asn Gly Ser Leu Glu Gln Gly Met
            115                 120                 125

Tyr Asn Thr Leu Glu Glu Trp Tyr Lys Phe Ile Glu Glu Ser Ile His
130                 135                 140

Val Gln Ala Asp Leu Ile Ile Tyr Leu Arg Thr Ser Pro Glu Val Ala
145                 150                 155                 160

Tyr Glu Arg Ile Arg Gln Arg Ala Arg Ser Glu Glu Ser Cys Val Pro
                165                 170                 175

Leu Lys Tyr Leu Gln Glu Leu His Glu Leu His Glu Asp Trp Leu Ile
                180                 185                 190

His Gln Arg Arg Pro Gln Ser Cys Lys Val Leu Val Leu Asp Ala Asp
                195                 200                 205

Leu Asn Leu Glu Asn Ile Gly Thr Glu Tyr Gln Arg Ser Glu Ser Ser
210                 215                 220

Ile Phe Asp Ala Ile Ser Ser Asn Gln Gln Pro Ser Pro Val Leu Val
225                 230                 235                 240

Ser Pro Ser Lys Arg Gln Arg Val Ala Arg
                245                 250

<210> SEQ ID NO 3
<211> LENGTH: 32
<212> TYPE: DNA
<213> ORGANISM: Drosophila melanogaster

<400> SEQUENCE: 3
aagaattcgg actgatggcg gaggcagcat cc                                      32

<210> SEQ ID NO 4
<211> LENGTH: 33
<212> TYPE: DNA
<213> ORGANISM: Drosophila melanogaster

<400> SEQUENCE: 4
aagtcgacgt actaatggga taatggttta tct                                     33

<210> SEQ ID NO 5
<211> LENGTH: 234
<212> TYPE: PRT
<213> ORGANISM: Homo sapiens

<400> SEQUENCE: 5

Met Gly Ala Phe Cys Gln Arg Pro Ser Ser Asp Lys Glu Gln Glu Lys
  1               5                  10                  15

Glu Lys Lys Ser Val Ile Cys Val Glu Gly Asn Ile Ala Gly Gly Lys
                 20                  25                  30

Thr Thr Cys Leu Glu Phe Phe Ser Asn Ala Thr Asp Val Glu Val Leu
             35                  40                  45

Thr Glu Pro Val Ser Lys Trp Arg Asn Val Arg Gly His Asn Pro Leu
         50                  55                  60

Gly Leu Met Tyr His Asp Ala Ser Pro Trp Gly Leu Thr Leu Gln Thr
 65                  70                  75                  80

Tyr Val Gln Leu Thr Met Leu Asp Arg His Thr Arg Pro Gln Val Ser
                 85                  90                  95

Ser Val Arg Leu Met Glu Arg Ser Ile His Ser Ala Arg Tyr Ile Phe
                100                 105                 110

Val Glu Asn Leu Tyr Arg Ser Gly Lys Met Pro Glu Val Asp Tyr Val
            115                 120                 125
```

-continued

```
Val Leu Ser Glu Trp Phe Asp Trp Ile Leu Arg Asn Met Asp Val Ser
    130                 135                 140

Val Asp Leu Ile Val Tyr Leu Arg Thr Asn Pro Glu Thr Cys Tyr Gln
145                 150                 155                 160

Arg Leu Lys Lys Arg Cys Arg Glu Glu Lys Val Ile Pro Leu Glu
                165                 170                 175

Tyr Leu Glu Ala Ile His His Leu His Glu Glu Trp Leu Ile Lys Gly
            180                 185                 190

Ser Leu Phe Pro Met Ala Ala Pro Val Leu Val Ile Glu Ala Asp His
        195                 200                 205

His Met Glu Arg Met Leu Glu Leu Phe Glu Gln Asn Arg Asp Arg Ile
    210                 215                 220

Leu Thr Pro Glu Asn Arg Lys His Cys Pro
225                 230

<210> SEQ ID NO 6
<211> LENGTH: 262
<212> TYPE: PRT
<213> ORGANISM: Homo sapiens

<400> SEQUENCE: 6

Met Ala Thr Pro Pro Lys Arg Ser Cys Pro Ser Phe Ser Ala Ser Ser
1               5                   10                  15

Glu Gly Thr Arg Ile Lys Lys Ile Ser Ile Glu Gly Asn Ile Ala Ala
                20                  25                  30

Gly Lys Ser Thr Phe Val Asn Ile Leu Lys Gln Leu Cys Glu Asp Trp
            35                  40                  45

Glu Val Val Pro Glu Pro Val Ala Arg Trp Cys Asn Val Gln Ser Thr
    50                  55                  60

Gln Asp Glu Phe Glu Glu Leu Thr Met Ser Gln Lys Asn Gly Gly Asn
65                  70                  75                  80

Val Leu Gln Met Met Tyr Glu Lys Pro Glu Arg Trp Ser Phe Thr Phe
                85                  90                  95

Gln Thr Tyr Ala Cys Leu Ser Arg Ile Arg Ala Gln Leu Ala Ser Leu
            100                 105                 110

Asn Gly Lys Leu Lys Asp Ala Glu Lys Pro Val Leu Phe Phe Glu Arg
        115                 120                 125

Ser Val Tyr Ser Asp Arg Tyr Ile Phe Ala Ser Asn Leu Tyr Glu Ser
    130                 135                 140

Glu Cys Met Asn Glu Thr Glu Trp Thr Ile Tyr Gln Asp Trp His Asp
145                 150                 155                 160

Trp Met Asn Asn Gln Phe Gly Gln Ser Leu Glu Leu Asp Gly Ile Ile
                165                 170                 175

Tyr Leu Gln Ala Thr Pro Glu Thr Cys Leu His Arg Ile Tyr Leu Arg
            180                 185                 190

Gly Arg Asn Glu Glu Gln Gly Ile Pro Leu Glu Tyr Leu Glu Lys Leu
        195                 200                 205

His Tyr Lys His Glu Ser Trp Leu Leu His Arg Thr Leu Lys Thr
    210                 215                 220

Asn Phe Asp Tyr Leu Gln Glu Val Pro Ile Leu Thr Leu Asp Val Asn
225                 230                 235                 240

Asn Glu Asp Phe Lys Asp Lys Tyr Glu Ser Leu Val Glu Lys Val Lys
                245                 250                 255

Glu Phe Leu Ser Thr Leu
```

260

<210> SEQ ID NO 7
<211> LENGTH: 277
<212> TYPE: PRT
<213> ORGANISM: Homo sapiens

<400> SEQUENCE: 7

Met Ala Ala Gly Arg Leu Phe Leu Ser Arg Leu Arg Ala Pro Phe Ser
 1               5                  10                  15

Ser Met Ala Lys Ser Pro Leu Glu Gly Val Ser Ser Arg Gly Leu
             20                  25                  30

His Ala Gly Arg Gly Pro Arg Arg Leu Ser Ile Glu Gly Asn Ile Ala
         35                  40                  45

Val Gly Lys Ser Thr Phe Val Lys Leu Leu Thr Lys Thr Tyr Pro Glu
     50                  55                  60

Trp His Val Ala Thr Glu Pro Val Ala Thr Trp Gln Asn Ile Gln Ala
 65                  70                  75                  80

Ala Gly Asn Gln Lys Ala Cys Thr Ala Gln Ser Leu Gly Asn Leu Leu
                 85                  90                  95

Asp Met Met Tyr Arg Glu Pro Ala Arg Trp Ser Tyr Thr Phe Gln Thr
            100                 105                 110

Phe Ser Phe Leu Ser Arg Leu Lys Val Gln Leu Glu Pro Phe Pro Glu
        115                 120                 125

Lys Leu Leu Gln Ala Arg Lys Pro Val Lys Ile Phe Glu Arg Ser Val
    130                 135                 140

Tyr Ser Asp Arg Tyr Ile Phe Ala Lys Asn Leu Phe Glu Asn Gly Ser
145                 150                 155                 160

Leu Ser Asp Ile Glu Trp His Ile Tyr Gln Asp Trp His Ser Phe Leu
                165                 170                 175

Leu Trp Glu Phe Ala Ser Arg Ile Thr Leu His Gly Phe Ile Tyr Leu
            180                 185                 190

Gln Ala Ser Pro Gln Val Cys Leu Lys Arg Leu Tyr Gln Arg Ala Arg
        195                 200                 205

Glu Glu Glu Lys Gly Ile Glu Leu Ala Tyr Leu Glu Gln Leu His Gly
    210                 215                 220

Gln His Glu Ala Trp Leu Ile His Lys Thr Thr Lys Leu His Phe Glu
225                 230                 235                 240

Ala Leu Met Asn Ile Pro Val Leu Val Leu Asp Val Asn Asp Asp Phe
                245                 250                 255

Ser Glu Glu Val Thr Lys Gln Glu Asp Leu Met Arg Glu Val Asn Thr
                260                 265                 270

Phe Val Lys Asn Leu
            275

<210> SEQ ID NO 8
<211> LENGTH: 31
<212> TYPE: DNA
<213> ORGANISM: Drosophila melanogaster

<400> SEQUENCE: 8
ttctcgagtg gttatctggc gaccctctgg c                               31

MEDICAL USE OF GENE AND VECTOR ENCODING A MULTISUBSTRATE DEOXYRIBONUCLEOSIDE KINASE

This is a national stage application under 35 U.S.C. 371 of PCT/SE99/01434, filed on Dec. 10, 1999, now abandoned.

The present invention relates to a gene encoding a multisubstrate deoxyribonucleoside kinase of *Drosophila melanogaster*, and vectors and recombinant viruses containing said gene, as well as pharmaceutical compositions comprising such a vector and/or a virus. It also relates to production of said multisubstrate deoxyribonucleoside kinase and a process for phosphorylating nucleosides and nucleoside analogs.

TECHNICAL BACKGROUND

Nucleoside analogs are commonly used in treatment of virus infections and cancer. The therapeutic nucleoside analogs are inactive prodrugs that are dependent on intracellular phosphorylation for pharmacological activity. The majority of nucleoside analogs in clinical use are phosphorylated by deoxyribonucleoside kinases (Arnér et al., (1995) *Pharmac. Ther.* 67, 155–186). These enzymes are intensively studied since they catalyze the rate limiting step in the pharmacological activation of the nucleoside analogs. There are four major deoxyribonucleoside kinases in human cells: deoxycytidine kinase (dCK), deoxyguanosine kinase (dGK), thymidine kinase 1 (TK1) and thymidine kinase 2 (TK2) (1995) *Pharmac. Ther.* 67, 155–186). DCK, dGK and TK2 are closely sequence-related enzymes whereas TK1 has low similarity with the other deoxyribonucleoside kinases (Johansson et al., (1996) *Proc. Natl. Acad. Sci. USA*. 93, 7258–7262; Johansson et al., (1997) *J. Biol. Chem.* 272, 8454–8458; Chottiner et al., (1991) *Proc. Natl. Acad. Sci. USA*. 88, 1531–1535). The human deoxyribonucleoside kinases have distinct substrate specificities in regard to phosphorylation of both deoxyribonucleosides as well as nucleoside analogs.

WO95/14102 discloses recombinant adenoviruses comprising a DNA sequence coding for herpes simplex thymidine kinase under the control of a heterologous expression signal that can be associated with certain form of cancer. These recombinant viruses are then used to infect tumours of such a cancer. As a result, thymidine kinase is expressed in the cancer tumour. Subsequently, a therapeutic nucleoside analog prodrug, such as acyclovir (ACV, 9-(hydroxy ethoxymethyl)-guanine) and gancyclovir (GCV), is administred. Due to the enhanced expression of thymidine kinase in the tumor, the prodrug is only converted to the active form in the tumour, resulting in death of the tumour. However, the ability of thymidine kinase to phosphorylate potentially useful nucleoside analog prodrugs is limited.

WO97/29196 also relates to recombinant adenoviruses comprising a DNA sequence encoding herpes simplex thymidine kinase (HSV-TK). The kinase is mutated in order to increase the phosphorylation rate and to broaden the substrate specificity.

WO96/21724 discloses recombinant virus particles, such as recombinant retroviruses, contaning RNA encoding human deoxycytidine kinase 2. These virus particles are used for the same purposes as the virus particles described in WO97/29196 and WO95/14102, but the enzyme has another substrate specificity.

Accordingly, it is known to insert a "suicide" nucleic acid sequence, such as a nucleic acid sequence encoding a nucleoside kinase, into the genome of a virus or some other kind of vector capable of transferring nucleic acid sequences into tumour cells of a human or animal patient, and subsequently administer a therapeutic nucleoside analog prodrug. Known nucleoside kinases have a limited substrate specificity. HSV-TK, which is described in the above cited WO97/29196 and WO95/14102, cannot phosphorylate 2',2'-difluorodeoxycytidine, 2-chloro-2'-deoxyadenosine, 1-β-D-arabinofuranosylcytosine, 2',3'-dideoxycytidine and 2'-deoxy-3-thiacytidine. Also deoxyguanosine kinase disclosed in the above cited WO96/2 1724 has been shown to have a limited substrate specificity. This enzyme does not phosphorylate), (E)-5-(2-bromovinyl)-2'-deoxyuridine, (E)-5-(2-bromovinyl)-1-β-D-arabinofuranosyl-uracil, 2',2'-difluorodeoxycytidine, 1-β-D-arabinofuranosylcytosine, 2',3'-dideoxycytidine or 3TC.

Consequently, there is a need for a DNA sequence encoding a nucleotide kinase having a broad specificity and a high catalytic rate of phosphozylation, in order to obtain flexibility regarding the use possible nucleoside analog prodrugs, and in order to reduce the dose amount required to obtain a sufficient therapeutic effect, resulting in a minimized risk for undesired side effects in the patient.

When comercially producing phosphoiylated nucleoside analogs., there is also a need for a nucleotide kinase having a broad specificity and a high catalytic rate of phosphorylation.

SUMMARY OF THE INVENTION

It has now turned out that by inserting a DNA or RNA sequence comprising a sub-sequence showing a homology of at least 60%, preferably at least 80%, and most preferably at least 90% of the DNA sequence of SEQ.ID.NO.1 into a cell, that cell will obtain a broad specificity for changing nucleoside analog prodrugs to active drugs by phosphorylation. Likewise this changement will occur at a high catalytic rate. Preferably the DNA sequence is inserted into the cell by transformation with a suitable virus or another suitable vector. Such viruses and vectors also constitute a part of the present invention.

DETAILED DESCRIPTION OF THE INVENTION

A recent report (Munch-Petersen et al., (1998) *J. Biol. Chem.* 273, 3926–3931) shows that cell lines from the fruit fly *Drosophila melanogaster* contains only a single deoxyribonucleoside kinase. The report does neither reveal anything about the aminoacid sequence of the enzyme, nor about any DNA sequence encoding it. This enzyme, namned DM-dNK, is in contrast to the human deoxyribonucleoside kinases a multisubstrate enzyme. Although pyrimidine nucleosides are the preferred substrates of this enzyme, it catalyzes phosphorylation of both pyrimidine and purine deoxyribonucleosides. The enzyme also efficiently phosphorylates several anti-viral and anti-cancer nucleoside analogs. The catalytic rates of deoxyribonucleoside and nucleoside analog phosphorylation are, depending on the substrate, 10- to 100-folds higher than the maximal catalytic rates reported for the mammalian enzymes. The broad substrate specificity and high catalytic rate in phosphorylation of deoxyribonucleosides render DM-dNK unique among the family members of deoxyribonucleoside kinases.

Accordingly, an object of the present invention is to provide a nucleic acid sequence encoding a multisubstrate deoxyribonucleoside kinase showing at least 70% homology, preferably at least 90% homology with the amino acid sequence of SEQ.ID.NO.2. Depending on the vector into which the nucleic acid sequence is intended to be inserted, the nucleic acid sequence can be a DNA sequence or a RNA sequence. The DNA may be cDNA, genomic DNA and synthetic DNA. It may also be double-stranded or single-stranded, and if single-stranded it may be the coding strand or the anti-sense strand. SEQ.ID.NO.1 discloses a cDNA sequence encoding the multisubstrate deoxyribonucleoside kinase. However, because of the fact that the genetic code is degenerated, other nucleic acid sequences encoding the same enzyme can be used in connection to the present invention.

Another object of the present invention is to provide a nucleic acid sequence comprising a disease-associated promoter and/or signal sequence operatively linked to a nucleic acid subsequence encoding a multisubstrate deoxyribonucleoside kinase showing at least 70% homology, preferably at least 90% homology with the amino acid sequence of SEQ.ID.NO.2. Depending on the vector into which the nucleic acid sequence is intended to be inserted, the nucleic acid sequence can be a DNA sequence or a RNA sequence. It is also possible to inject an expression cassette comprising such a DNA sequence directly into cells that are to be killed.

Yet another object of the present invention is to provide a vector, such as a plasmid, cosmid or a bacteriophage, which vector contains a DNA sequence encoding a multisubstrate deoxyribonucleoside kinase showing at least 70% homology, preferably at least 90% homology with the amino acid sequence of SEQ.ID.NO.2. Optionally, the vector also contains a disease-associated promoter and/or signal sequence operatively linked to the DNA sequence encoding a multisubstrate deoxyribonucleoside kinase. The invention also relates to host cells including these vectors.

Host cells are genetically engineered (transduced, transformed or transfected) with the vectors of this invention, which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes encoding the multisubstrate deoxyribonucleoside kinase. The culture conditions, such as temperature, pH and the like, are those previously used with the host cell selected for expression, and will be apparent for the skilled artisan.

The polynucleotides of the present invention may be employed for producing polypeptides by recombinant techniques. Thus, for example, the polynucleotide may be included in anyone of a variety of expression vectors for expressing a polypeptide. Such vectors include chromosomal, non-chromosomal (such as cDNA) and synthetic DNA sequences, e.g. derivatives of SV40, bacterial plasmids, phage DNA, baculovirus, yeast plasmids, vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequences may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli* lac (lacI, lacZ) or trp. the phage lambda $P_L$ promoter and other promoters known to control expression of genes in prokaryotic or eukaryotic cells or their viruses, such as the promoters T3, T7, gpt, lambda $P_R$, CMV immediate early, HSV thymidine kinase, early and late SV40 and late LTRs from retrovirus and mouse metallothionein-I. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

Yet another object of the present invention is to provide a process for producing a multisubstrate deoxyribonucleoside kinase by recombinant techniques comprising culturing recombinant prokaryotic and/or eukaryotic host cells containing and capable of expressing a nucleic acid sequence showing at least 70% homology, preferably at least 90% homology with the amino acid sequence of SEQ.ID.NO.2, under conditions promoting expression of said multisubstrate deoxyribonucleoside kinase and subsequent recovery of said multisubstrate deoxyribonucleoside kinase.

As representative examples of appropriate hosts, there may be mentioned: bacterial cells, such as *E. coli*, Streptomyces, *Salmonella typhimurium*; fungal cells, such as yeast; insect cells, such as Drosophila S2 and Spodoptera Sf9; animal cells such as CHO, COS or Bowes melanoma; adenovirus; plant cells etc. The selection of an appropriate host is deemed to be within the scope of those skilled in the art from the teachings herein.

Yet another object of the present invention is to provide a process for utilizing said multisubstiate deoxyribonucleoside kinase, or nucleic acid encoding such multisubstrate deoxyribonucleoside kinase, for example, to phosphorylate deoxyribonucleosides to ribonucleotides to activate specific anti-cancer and anti-viral drugs, and to preserve the fidelity of the deoxynucleotide pool.

Yet another object of the present invention is to provide a recombinant virus, such as a retrovirus or an adenovirus, whose genome comprises a disease-associated promoter and/or signal sequence operatively linked to a DNA sequence or a RNA sequence encoding a multisubstrate deoxyribonucleoside kinase showing at least 70% homology, preferably at least 90% homology with the amino acid sequence of SEQ.ID.NO.2.

Yet another object of the present invention is to provide a pharmaceutical comprising a recombinant virus, such as a retrovilus or an adenovirus, whose genome comprises a disease-associated promoter and/or signal sequence operatively linked to a DNA sequence or a RNA sequence encoding a multisubstrate deoxyribonucleoside kinase showing at least 70% homology, preferably at least 90% homology with the amino acid sequence of SEQ.ID.NO.2, together with a pharmaceutically acceptable carrier, excipient or diluent.

Yet another object of the present invention is to provide a conjugated multisubstrate deoxyribonucleoside kinase showing at least 70% homology, preferably at least 90% homology with the amino acid sequence of SEQ.ID.NO.2, which deoxyribonucleoside kinase is conjugated to a targeting group, such as a magnetic group or an antibody which specifically binds to an antigen associated with a disease, such as cancer or a virus infection.

Yet another object of the present invention is to provide a pharmaceutical composition comprising a conjugated multisubstrate deoxyribonucleoside kinase showing at least 70% homology, preferably at least 90% homology with the amino acid sequence of SEQ.ID.NO.2, which deoxyribonucleoside kinase is conjugated to a targetting group, such as a magnetic group or an antibody which specifically binds to an antigen associated with a disease, such as cancer or a virus infection, together with a pharmaceutically acceptable carrier, excipient or diluent.

As disclosed here, the term "multisubstrate deoxyribonucleoside kinase" relates to a deoxyribonucleoside kinase showing at least 70% homology, preferably at least 90% homology with the amino acid sequence of SEQ.ID.NO.2. The deoxyribonucleoside kinase is derived from *Drosophila melanogaster* and has a broad specificity for changing nucleoside analog prodrugs to active drugs by phosphorylation. Likewise this changement will occur at a high catalytic rate.

As disclosed herein, the terms "therapeutic nucleoside analog prodrug", "therapeutic nucleoside analog", and "nucleoside analog", relates to nucleosides and analogs of nucleosides which are non-toxic and/or lack useful pharmaceutical characteristics, but which are transformed to potent pharmaceutically useful compounds when they are phosphorylated. Typically, they become cytotoxic after such a phosphorylation. Examples of such compounds include 9-(hydroxyethoxymethyl)-guanine (ACV), 1-β-D-arabinofuranosyladenine (AraA), 1-β-D-arabinofuranosylcytosine (AraC), 1-β-D-arabinofuranosylguanine (AraG), 1-β-D-arabinofuranosylthymine (AraT), 3'-azido-2',3'-dideoxythymidine (AZT), 5-bromo-2'-deoxyuridine (BrdU), (E)-5-(2-bromovinyl)-2'-deoxyuridine (BVDU), 2-chloro-2'-deoxyadenosine (CdA), 2',3'-didehydro-2',3'-dideoxythymidine (D4T), 2',3'-dideoxycytidine (ddC), dideoxythymidine (ddT), 2',2'-difluorodeoxycytidine (dFdC), 1-(2-deoxy-2-fluoro-β-D-arabinofuranosyl)-5-iodouracil (FIAU), 3'-fluoro-2',3'-dideoxythymidine (FLT), (E)-5-(2-bromovinyl)-1-β-D-arabinofuranosyl-uracil (BVaraU), 5-fluorodeoxyuridine (FdU), and 2'-deoxy-3-thiacytidine, 2',2'-difluorodeoxyguanosine (dFdG), 2-fluoro-9-β-D-arabinofuranosyladenine (FaraA), 5-aza-2'-deoxycytidine (5-AzadC), 5-fluoro-2'-deoxycytidine (5-FdC), 5-methyl-deoxycytidine (5-metdC), granciclovir (GCV), 1-(2-deoxy-2-fluoro-1-β-D-abinofuranosyl)-5-thymine (FMAU) and 5-(2-bromovinyl)-2'-deoxycytidine BVDC).

As disclosed herein, the term "disease-associated promoter and/or signal sequence" relates to a promoter or a signal sequence that is active in a cell affected by a disease, such as cancer or a virus infection. It is not a requirement that the promoter controls a gene that actively causes the disease, but it is a requirement that the gene that is controlled by the promoter is active in a cell affected by the disease. Preferably, the gene is not active in surrounding cells not affected by the disease. Likewise, it is not necessary that the signal sequence is directly involved in the mechanisms behind the disease. However, it is a requirement that the signal sequence actively targets the gene encoding the multifunctional nucleoside kinase to a cell affected by the disease. Examples are promoters and signal sequences originating from viruses such as human immunodeficiency virus (HIV), hepatitis C virus (HIV), the promoter of the TK gene of herpes simplex virus type I, promoters of the adenovirus genes E1A, and MLP, the LTR promoter of Ross Sarcoma Virus, promoters of ubiquitous eucaryotic genes such as HPRT, PGK, alpha-actine, tubuline and DHFR, promoters from genes encoding filamentous proteins such as GFAP, desmine, vimentine, neurofilaments and keratine, promoters from therapeutically interesting genes such as MDR, CFTR, factor VIII, and ApoAI, promoters from genes that are specifically associated with certain tissues, such as the pyruvate kinase promoter, and promoters of intestinal fatty acid-binding proteins, promoters controlling the expression of oncogenes, etc. Signal sequences that can be used in relation to the present invention are nucleic acid sequences encoding a peptide sequence having the ability of directing the transport of a certain protein to the mitochondria (Zhu et al. (1998), *J. Biol. Chem.*, vol. 273, 14707–14711; Johansson et al. (1996), *Proc. Natl. Acad Sci. USA*, vol. 93, 7258–7262) or the cell nucleus (Johansson et al. (1997), *Proc. Natl. Acad. Sci. USA*, vol. 94, 11941–11945).

The invention also relates to novel pharmaceutical and therapeutic agents which render it possible to specifically kill cells affected by a certain disease, such as cancer or a virus infection. Expression cassettes comprising a cDNA encoding the multisubstrate deoxynucleoside kinase of the present invention operatively linked to a disease-associated promoter or a signal sequence can be directly injected per se into the tissue to be treated. However, it is preferred to use some kind of vector to introduce DNA into the cells to be treated. Examples of such vectors are DEAE-dextran (Pagano et al., (1967) J. Virol. Vol. 1, p.891), nucleai proteins (Kaneda et al., (1989) Science, Vol. 243, p. 375), lipids (Felgner et al., (1987) Proc. Natl. Acad. Sci. USA, vol. 84, p. 7413) and liposomes (Fraley et al., (1980) J. Biol. Chem. Vol. 255p. 10431).

In a preferred embodiment of the present invention, the DNA or RNA sequence is transferred to the cells by using a recombinant virus comprising a nucleic acid encoding the multisubstrate deoxynucleoside kinase of the present invention as a vector. Examples of such virus are retroviruses (RSV, HMS, MMS, etc) and adenovirus.

The expression cassette or the virus comprising a nucleic acid sequence encoding the multisubstrate deoxynucleoside kinase according to the present invention can be formulated into pharmaceutical compositions suitable for various administration routes, such as topical, oral, parenteral, intranasal, intraveneous, intramuscular, intraveneous, subcutanous, intraocular and transdermal administration. Preferably, the pharmaceutical compositions are used in an injectable form. Accordingly, the pharmaceutical compositions comprise an expression cassette or a virus containing a nucleic acid sequence encoding the multisubstrate deoxynucleoside kinase according to the present invention together with a pharmaceutically acceptable vehicle which is suitable for an injectable solution which preferably can be injected directly into the tissue to be treated. Examples of formulations are sterile isotonic aqueous solutions, or dry, in particular lyophilized, compositions which can be transformed into injectable solutions by adding e.g. sterile water or serum.

According to the present invention, cells may be engineered in vivo for expression of a polypeptide in vivo by, for example, procedures known in the art. As known in the art, a producer cell for producing a retroviral particle containing RNA encoding the polypeptide of the present invention may be administred to a patient for engineering cells in vivo and expression of the polypeptide in vivo. These and other methods for administering a multisubstrate deoxynucleoside kinase of the present invention by such method should be apparent to those skilled in the art from the teachings of the present invention. For example, the expression vehicle for engineering cells may be a retrovirus or an adenovirus which may be used to engineering cells in vivo after combination with a suitable delivery vehicle.

Once the multisubstrate deoxynucleoside kinase is being expressed intracellularly via gene therapy, it may be employed to treat malignancies, e.g. tumours, cancer, leukemias and lymphomas and viral infections, since the multisubstrate deoxynucleoside kinase catalyses the initial phosphorylation step of a therapeutic nucleoside analog prodrug. Examples of diseases that can be treated according to the principles outlined in the present application are: cancer in buccal cavity and pharynx, cancer in digestive organs (esophagus, stomach, small intestine, colon-rectum, liver, and biliary passages, pancreas), lung cancer, cancer of connective tissue, melanoma of skin, basal and squamous cell cancers, breast cancer, cancer in genital organs (cervix uteri, corpus uteri, ovary, prostate, testis), cancer in urinary organs (bladder, kidney), cancer of brain and central nervous system, cancer of endocrine glands (thyroid and other endocrine glands), leukemia and other cancers of blood and lymph tissues (Hodgkin's disease, Non-Hodgkins's lymphoma, multiple myeloma), human immunodeficiency virus (HIV) associated diseases, viral hepatitis, cytomegalovirus disease and other chronic infections caused by viruses.

A suitable dose of expression cassette or recombinant virus in relation to the present invention is a function of different parameters such as the vector/recombinant virus used, administration route, the particular pathology, or the duration of the treatment. A typical dose may be within the range from $10^9$–$10^{12}$ virus particles.

When the pharmaceutical composition comprising the expression cassette and/or the recombinant virus has been administred to suitable cells, these cells start to express the multisubstrate deoxyribonucleoside kinase. Then, a second pharmaceutical composition comprising a therapeutic nucleoside analog together with a pharmaceutically acceptable vehicle, excipient or diluent, preferably an injectable sterile aqueous solution is administred. The multisubstrate deoxyribonucleoside kinase according to the invention converts the therapeutic nucleoside analog to the active cytotoxic form resulting in cell death. A suitable dose of expression cassette or recombinant virus in relation to the present invention is a function of different parameters such as the vector/recombinant virus used, administration route, the particular pathology, or the duration of the treatment. A typical dose may be within the range of 100 mg–5000 mg.

BRIEF DESCRIPTION OF THE DRAWINGS

The invention will now be described with reference to the enclosed figures in which.

The invention will now be described with reference to the following examples, which are given for the purpose of illustration, and are not intended to limit the scope of the present invention.

EXAMPLE 1

Cloning of Dm-dNK cDNA

Figure 1:
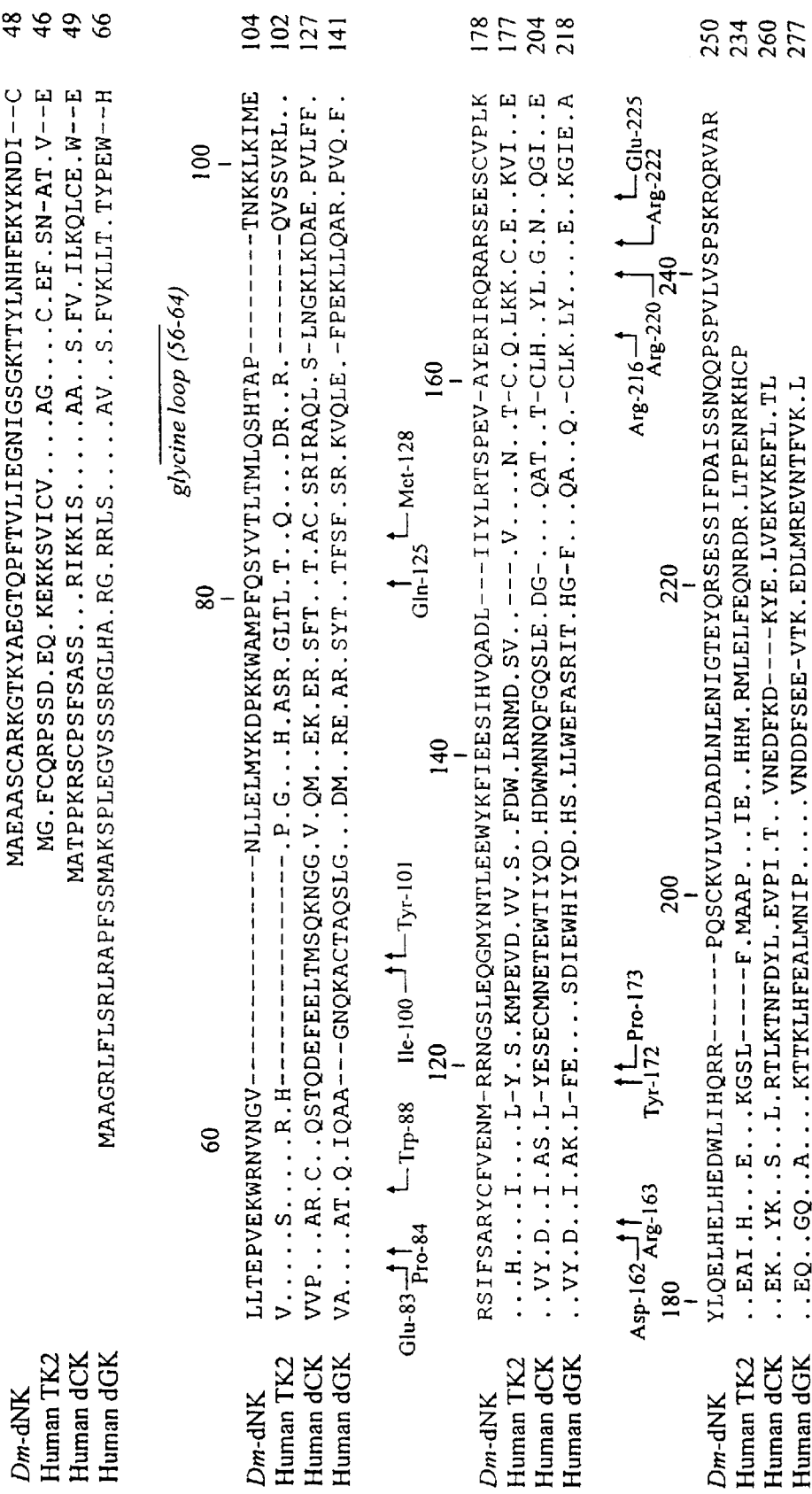
FIG. 1 shows similarities and homologies between the amino acid sequence of the kinase of the present invention (Dm-dNK) and human TK2, human dCK, and human dGK, respectively. The aminoacid sequences of these enzymes are aligned together and homologies are marked white text on black background.

The expressed sequence tag library of the GeneBank database at the National Institute for Biotechnology Information (http://www.ncbi.nlm.nih.gov/) was searched with the Basic Local Alignment Search Tool (BLAST) to identify *Drosophila melanogaster* cDNA clones that encoded enzymes similar to human dCK, dGK and TK2. An EST clone deposited by D. Harvey and coworkers (LD15983) was identified. A plasmid comprising the expressed sequence tag inserted in the vector pBluescript SK+/− (Sambrook et al., Molecular Cloning, Cold Spring Harbor Laboratory Press) was obtained from D. Harvey (Howard Hughes Medical Institute, University of California, USA) and the DNA sequence of the expressed sequence tag was confimed with an automatic laser fluorescent (A.L.F.) sequencer (Amersham Pharmacia Biotech) according to the manufacturer's instructions. The DNA sequence determination of the full length 1001 bp cDNA showed that it encoded a protein of 250 amino acid residues (SEQ.ID.NO.2). The calculated molecular mass of the protein was 29 kDa. The greatest similarity of the protein was to human TK2 that had 38% identical amino acids at best alignment (FIG. 1). Human dCK and dGK were both 28% identical to Dm-dNK.

EXAMPLE 2

Expression and Purification of Recombinant Dm-dNK

The cDNA-encoded protein was expressed in *Escherichia coli* as a fusion protein to glutathione-S-transferase. Two oligonucleotide primers that flanked the open reading frame of the cDNA were designed with EcoRI and SalI restriction enzyme sites (5'-AAGAATTCGGACTGATGGCGGAGGCAGCATCC (SEQ.ID.NO.3) and 5'-AAGTCGACGTACTAATGGGATAATGGTTATCT (SEQ.ID.NO.4)). The oligonucleotides were used in a PCR and the amplified DNA fragment was cloned into the EcoRI-SalI sites of the pGEX-5X-1 plasmid vector (Amersham Pharnacia Biotech). The plasmid was transformed into the *Escherichia coli* strain BL21(DE3)pLysS (Stratagene). A transformed colony was inoculated i 2YT medium (Sambrook., (1989) Molecular Cloning, Cold Spring Harbor Laboratory Press) supplemented with 100 μg/ml ampicillin and 34 μg/ml chloramphenicol. Protein expression was induced at $OD_{595}$=0.9 with 1 mM isopropyl-1-thio-β-D-galactopyranoside for 3 h at 37° C. The cells were harvested by centrifugation at 7,700×g for 10 min and resuspended in phosphate-buffered saline. The bacteria were lysed by addition of 1 mg/ml lysozyme and by sonication. Triton X-100 was added to a final concentration of 1% (v/v) and the sample was incubated for 30 min at room temperature. The protein extract was centrifuged at 12,000×g for 10 min and loaded onto a glutathione-Sepharose 4B column (Amersham Pharmacia Biotech). The purified recombinant protein was eluted in 50 mM Tris, pH 8.0 supplemented with 10 mM reduced glutathione (Sigma). The size and purity of the recombinant protein was determined by sodium dodecyl sulfate-polyacrylamide gel electrophoresis (Phast system, Amersham Pharmacia Biotech). The protein concentration was determined with Bradford Protein Assay (BIO-RAD) and bovine serum albumen was used as the concentration standard. About 10 mg of fusion protein per liter of bacterial culture was obtained. The electiophoresis showed a single band of the purified protein.

EXAMPLE 3

Characterization of Dm-dNK

A phosphor transferase assay was used to determine the substrate specificity of the putative deoxyribonucleoside kinase. The phosphoryl transfer assay was performed using [γ-$^{32}$P]ATP (3000 Ci/mmol. Amersham Pharmacia Biotech)

as described (Eriksson et al., (1991) *Biochem. Biophys. Res. Commun.*, vol. 176, pp. 586–592). The nucleosides were added to 50 mM Tris, pH 8, 5 mM MgCl$_2$, 1 mM unlabeled ATP, 100 µCi of [γ-$^{32}$P]ATP and 1 µg recombinant Dm-dNK. The samples were incubated 30 min at 37° C. 2 µl of the reaction mixtures were spotted on poly(ethyleneimine) cellulose F thin layer chromatography sheets (Merck Inc.) and the nucleotide separated in a buffer containing NH$_4$OH:isobutyric acid:dH$_2$O (1:66:33). The sheets were autoradiographed using phosphoimaging plates (BAS 1000, Fujix). Among the naturally occurring deoxyribonucleosides, the enzyme efficiently phosphorylated both the pyrimidines deoxycytidine and deoxythymidine as well as the purines deoxyadenosine and deoxyguanosine. The enzyme did not phosphorylate ribonucleosides. The results are disclosed in table 1 below:

TABLE 1

Substrate specificity of recombinant Dm-dNK.

| Substrate | Relative phosphorylation 100 µM |
|---|---|
| deoxyadenosine | 1.7 |
| deoxycytidine | 1.6 |
| deoxyguanosine | 1.5 |
| deoxythymidine | 1.0 |
| deoxyinosine | 0.0 |

The enzyme's phosphorylation of several nucleoside analogs was also studied. At 100 µM, all investigated nucleoside analogs were efficiently phosphorylated. It was also determined how efficiently the nucleoside analogs competed with deoxythymidine phosphorylation.

The competition experiments were carried out in the following way: The standard reaction mixture contained 2.5 mM MgCl$_2$, 10 mM dithio threitol, 1 mg/ml bovine serum albumin, 2.5 mM ATP, 10 mM NaF, 2 µM methyl-$^3$H-thymidine, an appropriate amount of a nucleoside analog and the multisubstrate deoxyribonucleoside kinase in an amount resulting in a linear conversion of the substrate, in a total reaction mixture of 50 µl of 50 mM Tris-HCl, pH 8.0. The reaction mixture was incubated at 37° C. for 30 min, and the reaction was terminated by spotting on to DE-81 discs (Whatman). The discs were instantly immersed and washed in ethanol (70%). The filters were dried and assayed for radioactivity in a tuluene-based scintillant. The concentration resulting in 50% inhibition of phosphorylation of 2 µM deoxythymidine was determined as a mean value of three independent experiments.

The results are presented in tables 2 and 3 below:

TABLE 2

Phosphorylation of nucleoside analogs by the multisubstrate deoxynucleoside kinase. The relative phosphorylation of the nucleoside analogs is correlated to deoxythymidine phosphorylation.

| Substrate | Relative phosphorylation at 100 µM substrate |
|---|---|
| AraA | 1.5 |
| AraC | 1.9 |
| AraG | 1.7 |
| AraT | 1.5 |
| AZT | 1.3 |
| BrdU | 4.0 |
| CdA | 1.8 |
| ddC | 1.6 |
| ddT | 1.9 |
| dFdC | 3.3 |

TABLE 2-continued

Phosphorylation of nucleoside analogs by the multisubstrate deoxynucleoside kinase. The relative phosphorylation of the nucleoside analogs is correlated to deoxythymidine phosphorylation.

| Substrate | Relative phosphorylation at 100 µM substrate |
|---|---|
| FdU | 1.5 |
| FLT | 1.7 |

TABLE 3

Nucleoside analog concentration resulting in 50% competitive inhibition (IC$_{50}$) of phosphorylation of 2 µM deoxythymidine by the multisubstrate deoxynucleoside kinase and HSV-1 TK

| Nucleoside analog | multisubstrate deoxynucleoside kinase (IC$_{50}$) | HSV-1 TK (IC$_{50}$) |
|---|---|---|
| BVaraU | 20 | 4 |
| AraC | 53 | >1000 |
| AraT | 84 | N.D. |
| AZT | 51 | N.D. |
| BVDU | 3 | 3 |
| CdA | 120 | >1000 |
| ddC | 755 | >1000 |
| ddT | 422 | N.D. |
| dFdC | 144 | >1000 |
| FdU | 25 | 58 |
| FIAU | 16 | 2 |
| FLT | 105 | N.D. |
| 3TC | 700 | >1000 |

N.D. = not determined

The table shows that the multisubstrate deoxynucleoside kinase of the invention is able to phosphorylate a large amount of nucleoside analogs. The previously used enzyme HSV-1 TK shows a more limited substrate specificity.

EXAMPLE 4

Construction of a Retrovirus Expressing Dm-dNK

TK-deficient osteosarcoma cells were obtained from the American Type Culture Collection. The cells were cultured in Dulbecco's Modified Eagle's Medium supplemented with 10% (v/v) fetal calf serum (Gibco BRL), 100 U/ml penicillin, and 0.1 mg/ml streptomycin. The cells were grown at 37° C. in a humidified incubator with a gas phase of 5% CO$_2$.

Figure 2:
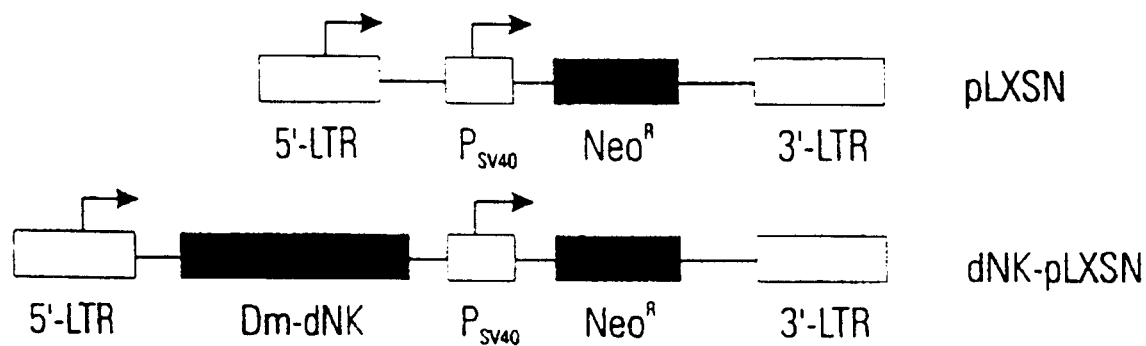
FIG. 2 presents retroviral vector pLXSN used to construct a retrovirus expressing Dm-dNK cDNA (dNK-pLXSN). LTR, $P_{SV40}$, and $Neo^R$, respectively, means long terminal repeat, SV40 large T-antigen promoter, and neomycine resistance gene, respectively.

A retrovirus vector based on the Moloney murine leukemia virus was used to generate a replicon-deficient recombinant retrovirus to introduce the cDNA of Dm-dNK in mammalian cells. Oligonucleotide primers containing engineered EcoRI and XhoI restriction enzyme sites were designed flanking the open reading frame of Dm-dNK cDNA (5'-AAGAATTCGGACTGATGGCGGAGGCAGCATCC (SEQ.ID.NO.4) and 5'-TTCTCGAGTGGTTATCTGGCGACCCTCTGGC (SEQ.ID.NO.8)). The primers were used in a PCR and the DNA fragment was cloned into the EcoRI-XhoI site of the pLXSN plasmid vector (Clontech). The plasmid was purified using the Nucleobond plasmid purification kit (Clontech). The DNA sequence of the constructed plasmid was verified by DNA sequence determination using a ABI310 automated DNA sequencer (Perkin-Elmer). FIG. 2 outlines replicon-deficient recombinant retroviridae with (dNK-pLXSN) and without the Dm-dNK cDNA (pLSNX).

RetroPack PT67 packaging cells (Clontech) were cultured in Dulbecco's Modified Eagle's Medium supplemented with 10% (v/v) fetal calf serum (Gibco BRL), 100 U/ml penicillin, and 0.1 mg/ml streptomycin. The pLXSN plasmid vectors were transfected into the packaging cells using LipofectAmine (Life Technology Inc.) according to the protocol provided by the supplier. 48 hours after transfection, medium from packaging cells were collected, filtered through a 0.45 µM filter, diluted 2-fold with fresh medium, and added to the osteosarcoma cells. Polybrene was added to the culture to a final concentration of 4 µg/ml. The cells were incubated for another 48 hours and then cultured for 3 weeks in the presence of 1.0 mg/ml Geneticin to generate a polpulation of stable transfected cells.

To verify that the Dm-dNK retained its enzymatic activity when expressed in human cells, the activity of dThd phosphorylation in crude cell protein extracts was determined. Cell protein extracts were prepared of the transfected osteosarcoma cells according to well-known methods. Deoxyribonucleoside kinase assays were performed in 50 mM Tris-HCl pH 7.6, 5 mM $MgCl_2$, 5 mM ATP, 5 mM dithiothreitol, 15 mM nAf, 100 mM KCl and 0.5 mg/ml bovine serum albumin. 2.5 µM unlabelled dThd, and 2.5 µM [8-$^3$H]-dThd (Moravek Biochemicals Inc.) or 2 µM unlabelled CdA and 3 µM [8-$^3$H]-CdA (Moravek Biochemicals Inc.) were added together with 20 µg of protein extract in a total volume of 35 µl. Aliquots of the reaction mixture were spotted on Whatman DE-81 filters after 10, 20 and 30 min incubation, respectively, at 37° C. The filters were washed three times in 50 mM ammonium formate, dTMP was eluted from the filter with 0.5 M KCl, and radioactivity was determined by scintillation counting.

Figure 4:
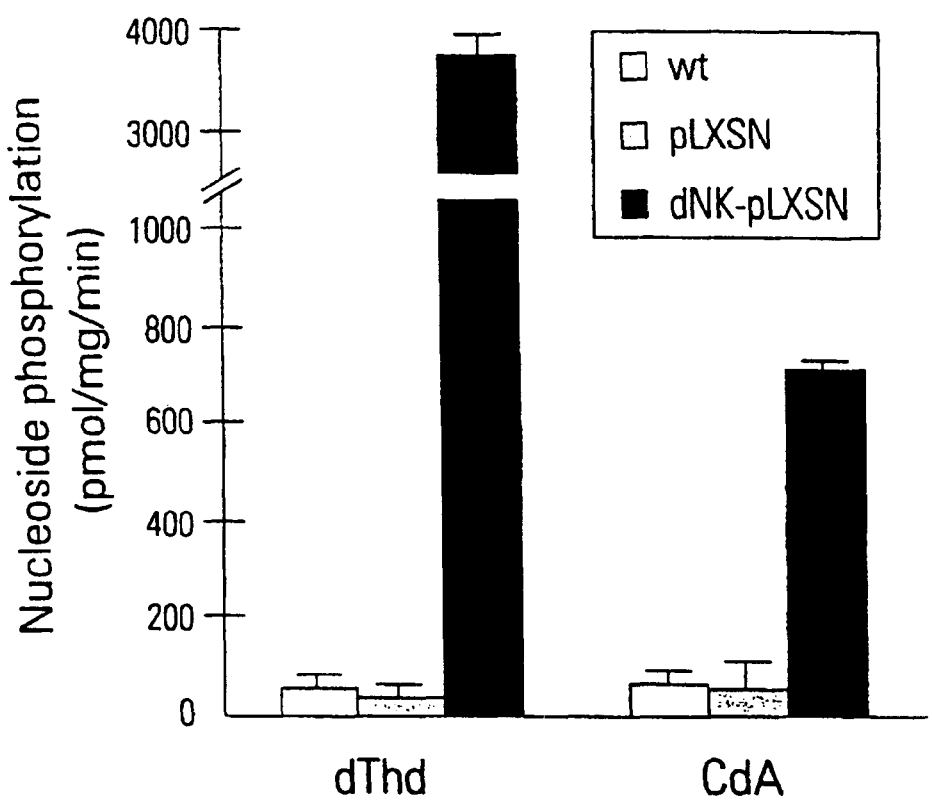
FIG. 4 is a diagram showing nucleoside kinase activity in crude extracts of cells expressing Dm-dNK. Phosphorylation of dThd and CdA were assayed.

The results are disclosed in FIG. 4. Untransfected osteosarcoma cells deficient in cytosolic TK1 expression showed low level of dThd phosphorylation, probably catalysed by mitochondrial TK2. The cells transfected with the pLXSN retroviral vector alone showed similar levels of dThd phosphorylation as the wild-type cells, whereas the cells transfected with dNK-pLXSN exhibited ~100-fold higher enzymatic activity than the parent cell line.

EXAMPLE 5

Western Blot and Autoradiography Using Mouse Polyclonal Antibodies

The Dm-dNK cDNA was expressed in the BL21 *E. Coli* strain with an N-terminal poly-histidine tag and the recombinant protein was purified by affinity chromatography. 2.0 µg protein diluted in 300 µl phosphate-buffered saline was injected subcutaneously in four-week-old female BALB/c mice with an equal volume of Freund's complete adjuvant (Sigma). A booster injection containing the same amount of protein was given ten days later together with Freund's incomplete adjuvant (Sigma). Two weeks after the booster injection, 3 ml of blood was retrieved and allowed to clot. The serum was collected and stored at −20° C.

To verify the specificity of the antibodies, a Western blot analysis was performed with recombinant Dm-dNK and the sequence-related human deoxyribonucleoside kinases dCK, dGK and TK2. Protein extracts of the transfected osteosarcoma cells in example 4. The protein concentration of the extracts was determined by Bio-Rad protein assay. The protein extracts were separated by 1.2% SDS/PAGE gel electrophoresis. The proteins were electrotransferred to a nitrocellulose membrane at 35 V overnight. The membranes were blocked for 1 h at room temperature with the Dm-dNK mouse antisera and washed three times with TBS buffer. A secondary alkaline phosphatase conjugated anti-mouse IgG antibody diluted 1:5000 (Sigma) was applied for 1 h and the membrane was washed in TBS buffer. The alkaline phosphatase immobilised on the membrane was developed with BCIP/NBT (Sigma).

Figure 3:
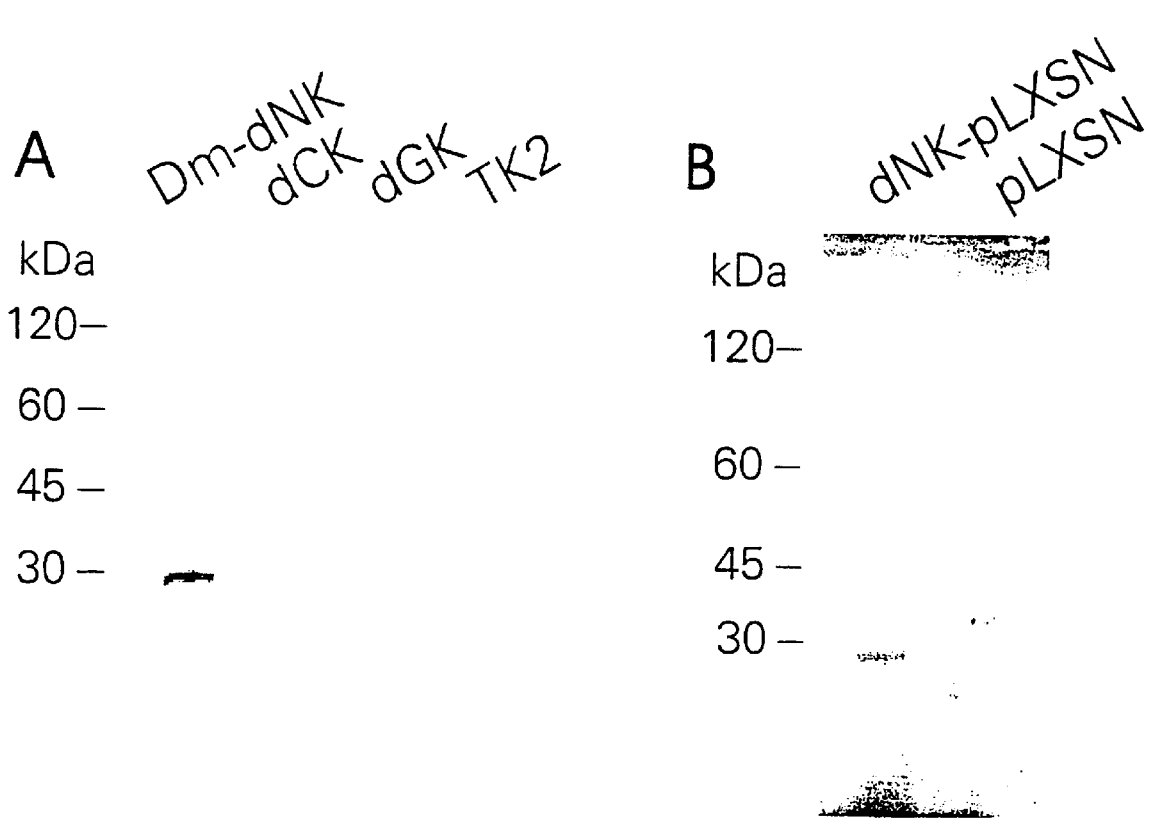
FIG. 3 discloses Western blot analysis of Dm-dNK expression in cancer cells with mouse polyclonal anti-Dm-dNK antibodies. (A) The antibodies detected recombinant Dm-dNK and without any cross-reactivity to the human nucleoside kinases dCK, dGK, and TK2. (B) Western blot analysis of protein extracts from osteosarcoma cell lines transfected with the pLXSN vector or the vector expressing Dm-dNK.

The results of the Western blot analysis are shown in FIG. 3A. The anti-Dm-dNK antibodies detected the Dm-dNK protein and did not cross-react with the human nucleoside kinases. The antibodies were used to analyse the expression of Dm-dNK in the transfected cells (FIG. 3B). A band of 28 kDa was detected in the cells transduced with the dNK-pLXSN vector, but not in the cells transduced with pLSNX.

Autoradiography was further used to visualise incorporation of dThd in situ. The cells were cultured on poly-L-lysine-coated chamber slides (Nunc, Inc.) for 24 h. Cells were labelled with [$^3$H]-dThd (Moravek Biochem) for 12 hours. The slides were rinsed with PBS twice, fixed ten minutes in methanol:acetic acid (3:1), washed three times with ice-cold 10% TCA, and then air-dried. The slides were coated with photoemulsion (Amersham) and exposed 1–4 weeks at 4° C. The autoradiographs were developed using a developer.

Figure 5:
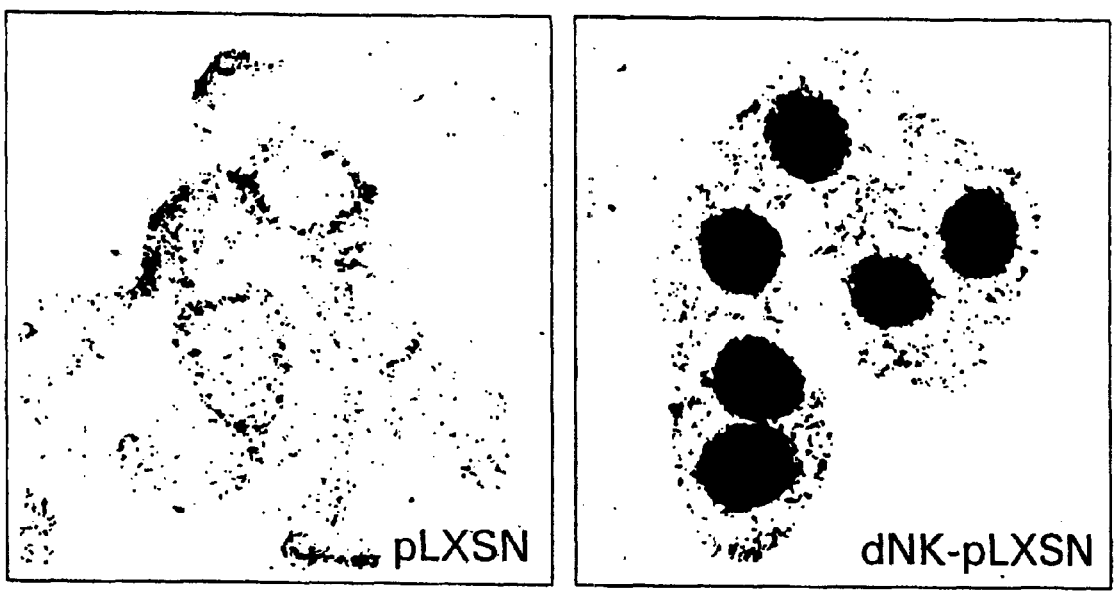
FIG. 5 present autoradiographies of TK-deficient cells transduced with pLXSN or dNK-pLXSN incubated with $^3$H-dThd. Wt means wild-type.

The results of the autoradiography are presented in FIG. 5. The TK-deficient cells incubated with [$^3$H]-dThd showed a dotted autoradiography pattern distributed throughout the cells, indicating phosphorylation of dThd by mitochondrial TK2 and its subsequent incorporation into mitochondrial DNA. The cells expressing Dm-dNK exhibited incorporation of [$^3$H]-dThd into nuclear DNA. ~90% of the cells in the population showed this pattern, indicating that the majority of cells expressed the Dm-dNK. In summary, the experiments described in examples 4 and 5 show that cancer cells infected with the dNK-pLXSN retroviral vector express Dm-dNK and that the enzyme retained its enzymatic activity when expressed in human cells.

EXAMPLE 6

Cell Proliferation Assays

The sensitivities of the transduced cancer cells to the nucleoside analogs BVDU, FdUrd, araC and dFdC were determined. AraC, and FdUrd were obtained from Sigma Inc. DFdC and dFdG were obtained from Lilly Research Laboratories. BVDU was a gift from Prof J. Balzarini, Leuven, Belgium. 2000 cells were plated in 96-well microtiter plates and indicated concentrations of nucleoside analogs were added after 24 h. Cell survival was assayed by the MTT assay (Boehringer Mannheim) after four days of drug exposure. Each experiment was performed in triplicate. Statistical analysis was performed using the student's paired t test.

Figure 6:
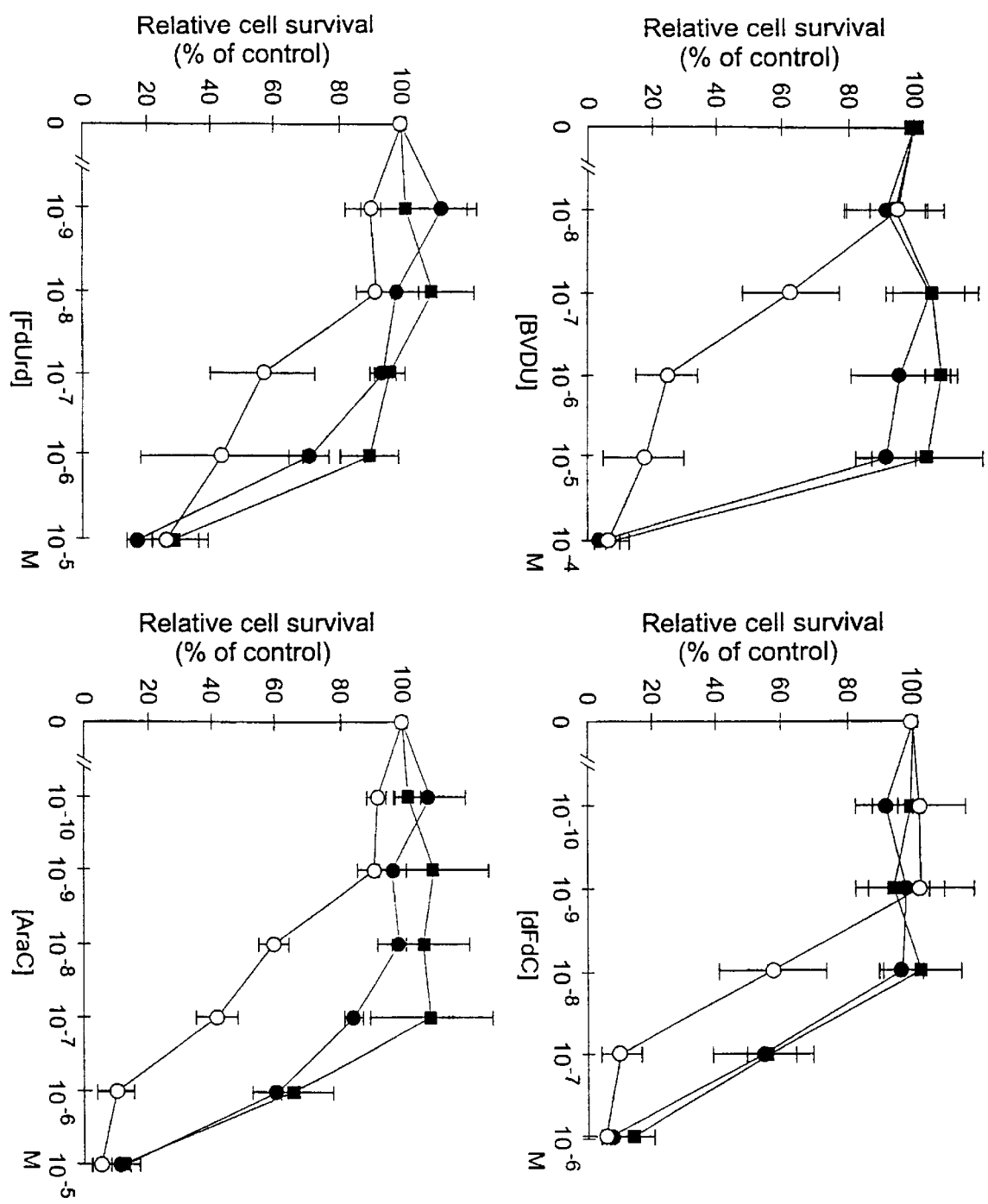
FIG. 6 discloses diagiams showing sensitivity of osteosarcoma cells to the nucleoside analogs BVDU, FdUrd, araC and dFdC.

The results are disclosed in FIG. 6. The wild-type parent cell line is represented by filled circles, cells transduced with pLXSN vector alone is represented by filled squares, and cells transduced with dNK-pLXSN is represented by open circles. The diagrams of FIG. 6 show that the wild-type parent cell line and cells transduced with the LXSN vector alone were equally sensitive to the investigated nucleoside analogs. The cells transduced with dNK-LXSN showed 10- to 1000-fold higher sensitivity to BVDU, FdUrd, araC and dFdC.

What is claimed is:

1. A nucleic acid sequence encoding a multisubstrate deoxyribonucleoside kinase having a sequence showing at least 70% homology with the amino acid sequence of SEQ ID NO:2, for medical use.

2. A nucleic acid sequence according to claim 1, wherein the multisubstrate deoxyribonucleoside kinase has an amino acid sequence according to SEQ ID NO:2, for medical use.

3. A nucleic acid sequence according to claim 1, wherein the nucleic acid sequence shows at least 70% homology with the nucleotide sequence of SEQ ID NO:1, for medical use.

4. A vector comprising a nucleic acid sequence according to claim 1, for medical use.

5. A vector according to claim 4, wherein said nucleic acid sequence is functionally linked to a disease-associated promoter and/or signal sequence.

6. A recombinant virus comprising a nucleic acid sequence according to claim 1.

7. A recombinant virus according to claim 6, wherein said nucleic acid sequence is functionally linked to a disease-associated promoter and/or signal sequence.

8. A recombinant virus according to claim 7, for medical use.

9. A nucleic acid sequence encoding a multisubstrate deoxyribonucleoside kinase comprising a sequence showing at least 90% homology with the amino acid sequence of SEQ ID NO:2.

10. A nucleic acid sequence according to claim 9, wherein the nucleic acid sequence shows at least 90% homology with the nucleotide sequence of SEQ ID NO:1.

11. A nucleic acid sequence according to claim 9, which is a DNA sequence.

12. A nucleic acid sequence according to claim 9, which is a RNA sequence.

13. A cloning vector comprising a nucleic acid sequence according to claim 9.

14. A host cell genetically engineered with a cloning vector according to claim 13.

15. An expression vector comprising a nucleic acid sequence according to claim 9.

16. A host cell genetically engineered with an expression vector according to claim 15.

17. A recombinant virus comprising a nucleic acid sequence according to claim 9.

18. A pharmaceutical composition comprising a vector according to claim 5 or a recombinant virus according to claim 7, together with a pharmaceutically acceptable carrier, excipient and/or diluent.

19. A method for producing a multisubstrate deoxyribonucleoside kinase comprising the steps of inserting a vector according to claim 4 into a suitable procaryotic or eucaryotic host cell, culturing said host cell under conditions causing expression of said multisubstrate deoxyribonucleoside kinase and subsequently recovering said multisubstrate deoxyribonucleoside kinase from the host cell or the culture medium.

* * * * *